(12) United States Patent
Röder et al.

(10) Patent No.: US 8,718,996 B2
(45) Date of Patent: *May 6, 2014

(54) METHOD FOR PREDICTING WHETHER A CANCER PATIENT WILL NOT BENEFIT FROM PLATINUM-BASED CHEMOTHERAPY AGENTS

(71) Applicant: Biodesix, Inc., Boulder, CO (US)

(72) Inventors: Joanna Röder, Steamboat Springs, CO (US); Heinrich Röder, Steamboat Springs, CO (US); Julia Grigorieva, Steamboat Springs, CO (US)

(73) Assignee: Biodesix, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/836,064

(22) Filed: Mar. 15, 2013

(65) Prior Publication Data

US 2014/0012514 A1    Jan. 9, 2014

Related U.S. Application Data

(60) Provisional application No. 61/668,077, filed on Jul. 5, 2012.

(51) Int. Cl.
| | | |
|---|---|---|
| *G01N 33/48* | (2006.01) | |
| *G01N 33/50* | (2006.01) | |
| *G06G 7/58* | (2006.01) | |
| *G06G 7/48* | (2006.01) | |
| *G06F 19/00* | (2011.01) | |

(52) U.S. Cl.
CPC .......... *G06F 19/3437* (2013.01); *G06F 19/345* (2013.01)
USPC .................................. 703/11; 702/19; 702/22

(58) Field of Classification Search
None
See application file for complete search history.

(56) References Cited

U.S. PATENT DOCUMENTS

| | | | |
|---|---|---|---|
| 7,736,905 B2 | 6/2010 | Roder et al. | |
| 7,858,389 B2 | 12/2010 | Roder et al. | |
| 7,858,390 B2 | 12/2010 | Roder et al. | |
| 7,867,775 B2 | 1/2011 | Roder et al. | |
| 7,879,620 B2 | 2/2011 | Roder et al. | |
| 7,906,342 B2 | 3/2011 | Roder et al. | |
| 7,951,405 B2 * | 5/2011 | Higgins et al. | 424/649 |
| 8,024,282 B2 | 9/2011 | Tsypin et al. | |
| 8,097,469 B2 * | 1/2012 | Roder et al. | 436/173 |
| 2003/0108545 A1 * | 6/2003 | Rockwell et al. | 424/143.1 |
| 2010/0055100 A1 | 3/2010 | Röder | |
| 2010/0145893 A1 * | 6/2010 | Semizarov et al. | 706/12 |
| 2011/0208433 A1 | 8/2011 | Grigorieva et al. | |
| 2012/0193525 A1 | 8/2012 | Roder et al. | |

OTHER PUBLICATIONS

Zhang et al., "Biomarker discovery of ovarian cancer using SELDI-TOF-MS", Gynecologic Oncology, 102:61-66 (2006).
Han et al., "Identification of candidate molecular markers predicting chemotherapy resistance in non-small cell lung cancer", Clin. Chem. Lab. Med. 48(6):863-867 (2010).
Helgason et al., "Identification of serum proteins as prognostic and predictive markers of colorectal cancer using surface enhanced laser desorption ionization-time of flight mass spectrometry", Oncology Reports, 24:57-64 (2010).
Voortman et al., "Prediction of outcome of non-small cell lung cancer patients treated with chemotherapy and bortezomib by time-course MALDI-TOF-MS serum peptide profiling", BioMed Central, 7(1):1-14 (2009).
International Search Report dated Jun. 17, 2013, for corresponding PCT application No. PCT/US2013/032010.
Rosell et al., "Pharmacogenomics and gemcitabine", Annals of Oncology, 17:13-16 (2006).
Vansteenkiste et al., Abstract of Assessment of VeriStrat as a predictive biomarker in a Phase 3 study of gemcitabine (G) + cisplatin (C) sorafenib in first line Stage IIIB or IV NSCLCm, ASCO Meeting Abstract, May 2012.
de Visser and Jonkers, "Towards Understanding the Role of Cancer-Associated Inflammation in Chemoresistance", Current Pharmaceutical Design, 15:1844-1853 (2009).
Lee et al., "Inflammation in Lung Carcinogenesis: New Targets for Lung Cancer Chemoprevention and Treatment", Crit. Rev. Oncol. Hematol. 66(3):208-217 (2008).
Martin et al., "Platinum Resistance: The Role of DNA Repair Pathways", Clin. Cancer Res. 14(5):1291-1295 (2008).
Mercer et al., "Rapid up-regulation of cycloxygenase-2 by 5-fluorouracil in human solid tumors", Preclinical Report, p. 495-500 (2005).
Xiao et al., "Serum Proteomic Profiles Suggest Celecoxib-Modulated Targets and Response Predictors", Cancer Research, 64:2904-2909 (2004).

(Continued)

*Primary Examiner* — Russell S Negin
(74) *Attorney, Agent, or Firm* — McDonnell Boehnen Hulbert & Berghoff LLP (57) ABSTRACT

A testing method for identification whether a cancer patient is a member of a group or class of cancer patients that are not likely to benefit from administration of a platinum-based chemotherapy agent, e.g., cisplatin, carboplatin or analogs thereof, either alone or in combination with other non-platinum chemotherapy agents, e.g., gemcitabine and paclitaxel. This identification can be made in advance of treatment. The method uses a mass spectrometer obtaining a mass spectrum of a blood-based sample from the patient, and a computer operating as a classifier and using a stored training set comprising class-labeled spectra from other cancer patients.

10 Claims, 6 Drawing Sheets

(56) References Cited

OTHER PUBLICATIONS

Taguchi et al., "Mass Spectrometry to Classify Non-Small-Cell Lung Cancer Patients for Clinical outcome After Treatment with Epidermal Growth Factor Receptor Tyrosine Kinase Inhibitors: A Multicohort Cross-Institutional Study", J. Nat. Cancer Institute 99:838 (2007).

Carbone D., et al., "Serum Proteomic Prediction of Outcomes in Advanced NSCLC Patients Treated With Erlotinib/Placebo in the NCIC Clinical Trials Group BR.21 Trial", 2nd European Lung Cancer Conference, Apr. 2010. J. Thorac. Oncol. 2010; 5(5) S80 abstract 203O.

Chung et al., "Detection of Tumor Epidermal Growth Factor Receptor Pathway Dependence by Serum Mass Spectrometry in Cancer Patients", Cancer Epidemiol Biomarkers Prev. 2010. 19(2):358.

* cited by examiner

Fig. 1

KAPLAN-MEIER PLOT OF PFS BY VERISTRAT
GROUP IN THE GEMCITABINE ARM

Fig. 2

KAPLAN-MEIER PLOT OF OS BY VERISTRAT
GROUP IN THE GEMCITABINE ARM

Fig. 3

KAPLAN-MEIER PLOT OF TTP FOR GROUPS VERISTRAT GOOD ('GOOD') AND VERISTRAT POOR ('POOR') FOR ADVANCED NSCLC PATIENTS TREATED WITH CISPLATIN-BASED CHEMOTHERAPY AS FIRST LINE TREATMENT.

Fig. 4

KAPLAN-MEIER PLOT OF OS FOR GROUPS VERISTRAT GOOD AND VERISTRAT POOR FOR ADVANCED NSCLC PATIENTS TREATED WITH CISPLATIN-BASED CHEMOTHERAPY AS FIRST LINE TREATMENT.

Fig. 6

SURVIVAL OF NSCLC PATIENTS TREATED WITH
DOCETAXEL: OS

Fig. 7A

DISEASE FREE SURVIVAL FOR OVARIAN CANCER PATIENTS
TREATED WITH CARBOPLATIN AND PACLITAXEL AFTER SURGERY

| | |
|---|---|
| LOG-RANK (MANTEL-COX) TEST | |
| P VALUE | 0.0512 |
| MEDIAN SURVIVAL | |
| VERISTRAT GOOD | 20.00 |
| VERISTRAT POOR | 11.00 |
| HAZARD RATIO | |
| RATIO | 0.4906 |
| 95% CL OF RATIO | 0.2398 TO 1.004 |

Fig. 7B

Overall survival for ovarian cancer patients treated with carboplatin and paclitaxel after surgery

METHOD FOR PREDICTING WHETHER A CANCER PATIENT WILL NOT BENEFIT FROM PLATINUM-BASED CHEMOTHERAPY AGENTS

CROSS-REFERENCE TO RELATED APPLICATION

This application claims priority benefits under 35 U.S.C. §119(e) to U.S. provisional application Ser. No. 61/668,077 filed Jul. 5, 2012, the entire content of which is incorporated by reference herein.

BACKGROUND

This invention relates generally to the field of methods for guiding the treatment of cancer patients with chemotherapy agents. More particularly, this invention relates to a method of predicting, in advance of initiating treatment, whether a patient is a member of a class of patients that are unlikely to benefit from administration of platinum-based chemotherapy agents, such as cisplatin, carboplatin, and analogs thereof. The methods of this disclosure use mass spectral data obtained from a blood-based sample of the patient, a computer configured as a classifier operating on the mass spectral data, and a training set comprising class-labeled spectra from other cancer patients.

The assignee of the present invention, Biodesix, Inc., has developed a test known as VeriStrat. One of the uses of VeriStrat is that it predicts whether Non-Small Cell Lung Cancer (NSCLC) patients are likely or not likely to benefit from treatment with drugs targeting the Epidermal Growth Factor Receptor (EGFR) pathway, e.g. EGFR inhibitors such as erlotinib. The test is described in U.S. Pat. No. 7,736,905, the content of which is incorporated by reference herein. Additional applications of the test are also described in U.S. Pat. Nos. 7,858,390; 7,858,389 and 7,867,775, the contents of which are incorporated by reference herein.

In brief, the VeriStrat test is based on serum and/or plasma samples of cancer patients. Through a combination of MALDI-TOF mass spectrometry and data analysis algorithms implemented in a computer, the commercial version of the test compares a set of eight integrated peak intensities at predefined m/z ranges in the mass spectrum of the patient sample (after pre-processing steps are performed) with those from a training cohort, and generates a class label for the patient sample: either VeriStrat Good, VeriStrat Poor, or VeriStrat "indeterminate." In multiple clinical validation studies it has been shown that patients, whose pre-treatment serum/plasma is classified as VeriStrat Good, have significantly better outcome when treated with epidermal growth factor receptor inhibitor drugs than those patients whose sample is classified as VeriStrat Poor. In a few cases (less than 2%) no determination can be made, resulting in a VeriStrat indeterminate label.

The applicants have further discovered that the VeriStrat test is also predictive for whether head and neck squamous cell carcinoma and colorectal cancer patients are likely to have better or worse outcomes from treatment with certain anti-cancer drugs, as described in U.S. Pat. Nos. 8,024,282; 7,906,342; 7,879,620; 7,867,775; 7,858,390; 7,858,389 and 7,736,905.

In pending U.S. patent application Ser. No. 13/356,730 filed Jan. 24, 2012, we have described how the VeriStrat test also predicts that breast cancer patients having the VeriStrat Poor signature are unlikely to obtain good clinical outcomes from endocrine therapy alone, including for example an aromatase inhibitor such as letrozole. In that document, we have also described how hormone receptor positive breast cancer patients, regardless of their HER2 status, which have the VeriStrat Poor signature are likely to benefit from administration of a combination treatment comprising administration of a targeted anti-cancer drug in addition to an endocrine therapy drug.

Platinum-based chemotherapy drugs, including cisplatin (cis-$PtCl_2(NH_3)_2$) and analogs thereof, are used to treat various kinds of cancers, including sarcomas, lymphomas, and carcinomas. The drug reacts in vivo, binding to and causing crosslinking of DNA, which interferes with cell division by mitosis, ultimately triggering apoptosis (programmed cell death). Cisplatin combination therapy is a cornerstone of treatment of many cancers. However, while initial platinum responsiveness is high, some patients do not respond to treatment, and the majority of cancer patients will eventually relapse with cisplatin resistant disease. There is a need in the art to be able to predict in advance of treatment whether a patient will not obtain benefit from cisplatin (alone or in combination treatment) as if this determination can be made at an early stage in treatment the patient can be guided towards other non-platinum therapies that are more likely to provide clinical benefit. This invention meets that need.

SUMMARY

We have discovered that our mass spectral test described in the above-referenced documents can be used to identify whether a cancer patient is a member of a class of cancer patients that are not likely to benefit from platinum-based chemotherapy agents such as cisplatin, carboplatin, or analogs thereof, either alone or in combination with other non-platinum-based anticancer agents, e.g., anti-mitotic agents such as docetaxel or nucleoside analogs such as gemcitabine. Such patients are identified when the classifier assigns the Poor class label to the sample's mass spectrum.

These discoveries are implemented in the form of practical, concrete and useful tests. One example is a testing method which identifies, in advance of treatment, whether a particular cancer patient (e.g., NSCLC, ovarian cancer patient) is a member of a group or class of cancer patients that are not likely to benefit from administration of a platinum-based chemotherapy agent, e.g., cisplatin, carboplatin or analogs thereof, either alone or in combination with other non-platinum chemotherapy agents. If the patient is identified as being a member of this group (by virtue of having the Poor class label), the patient is directed towards an anticancer treatment regimen that does not contain platinum-based chemotherapy agents. Accordingly, the patient is steered at the outset away from treatments that are not likely to benefit the patient and towards other treatment options that are more likely to provide some clinical benefit.

One embodiment of the test is in the form of a method for guiding treatment of a NSCLC patient. The method includes the steps of: a) obtaining a blood-based sample from the patient; b) obtaining a mass-spectrum of the blood-based sample with the aid of a mass spectrometer; and c) in a programmed computer, performing 1) predefined pre-processing steps on the mass spectrum (e.g., background subtraction, normalization and spectral alignment), 2) obtaining integrated intensity values of selected features at one or more predefined m/z ranges in the spectrum after the pre-processing steps are performed, and 3) comparing the integrated intensity values with a training set comprising class-labeled spectra from other cancer patients and thereby classifying the mass spectrum with a class label. This step 3) is a classification step and can be implemented in various ways, including with the aid of a K-nearest neighbor classification algorithm implemented in the computer as described below. The method further includes step d), wherein if the class label is Poor or the equivalent, the patient is predicted to not benefit from treatment in the form of administration of a platinum-based chemotherapy agent and is thereby guided towards a treatment regimen not containing platinum agents.

In a variation of the method, at step d) if the class label is Poor or the equivalent, the patient is predicted to not benefit from treatment in the form of administration of a combination of a non-platinum chemotherapy agent and a platinum-based chemotherapy agent and the patient is guided towards treatment regimen not containing platinum agents.

While we describe specific data supporting this invention in the context of non-small cell lung cancer and ovarian cancer, our previous work in this field across many different types of cancer (see the above-cited patent documents and the application of Julia Grigorieva et al., U.S. Ser. No. 12/932,295 filed Feb. 22, 2011) leads us to conclude that the VeriStrat test is also predictive for cancer patient non-benefit from platinum-based chemotherapy in general; i.e., that those cancer patients having the VeriStrat Poor signature generally are not likely to benefit from platinum-based chemotherapy agents. That is, the method recited above can be performed on blood-based samples of cancer patients and if the class label is Poor or the equivalent the patient is predicted to not benefit from treatment in the form of administration of a platinum chemotherapy agent, a combination of platinum chemotherapy agents, or combinations of a non-platinum chemotherapy agent and a platinum-based chemotherapy agent, and the patient is thereby guided towards a treatment regimen not containing platinum agents.

DETAILED DESCRIPTION

I. Predictive Tests for Platinum-Based Chemotherapy Agents, Related Classifiers and Systems The discovery that the VeriStrat test is predictive of cancer patients not benefitting from platinum based chemotherapy agents resulted from our analysis of VeriStrat separation of survival curves in patients enrolled in an ovarian cancer study, and in two separate lung cancer studies, one of which involved a study of elderly NSCLC patients treated with gemcitabine and a second study of advanced NSCLC patients receiving cisplatin-based chemotherapy as first line treatment. In this second study, most of the patients were known to have received cisplatin in combination with gemcitabine. The first lung cancer study will be referred to as "the LCCC0512 study" and the second lung cancer study will be referred to as "the Italian study." Our results from analysis of the ovarian cancer study and both lung cancer studies are described below.

In both the ovarian cancer study and the lung cancer studies, our work involved obtaining plasma or serum samples from patients enrolled in the studies, obtaining mass spectra of such samples, performing certain pre-processing steps on the spectra, and then subjecting the spectra to a classifier we have developed and described in our U.S. Pat. No. 7,736,905. The classifier assigned a class label to the samples, either Good or Poor or in a few instances "indeterminate." The class labels for the patient samples were assigned using a K-nearest neighbor (K-NN) classification algorithm based on a comparison of the spectra, after preprocessing and calculation of integrated intensity values of selected features at one or more predefined m/z ranges in the spectra, with a training set of class-labeled spectra from other cancer patients.

In our work, the training set used by the classification algorithm consisted of class-labeled spectra from a population of non-small cell lung cancer patients, with the class-label for a spectrum in the training set being Good if the associated patient benefitted from administration of an epidermal growth factor receptor inhibitor (EGFR-I) in the treatment of NSCLC, whereas the class label Poor was assigned to spectra for patients who did not benefit from such drugs. This training set and the classifier were the subject of extensive validation studies. The method of conducting our mass-spectral testing and classification of blood-based samples is explained in further detail below.

The LCCC0512 study was a randomized phase II trial of first-line treatment with gemcitabine, erlotinib or the combination in elderly (over 70 years old) patients with advanced non-small cell lung cancer (NSCLC). Patients had stage IIIB or IV NSCLC and ECOG performance status of 0-2. Patients were randomized to receive either a maximum of 4 cycles of gemcitabine (1200 mg/m$^2$ days 1,8 every 21 days), 150 mg erlotinib daily, or a maximum of 4 cycles of gemcitabine (1000 mg/m$^2$ days 1,8 every 21 days) with concurrent 100 mg erlotinib daily. Primary endpoint was progression-free survival at 6 months. Patients randomized to receive gemcitabine monotherapy were encouraged to continue on study to receive erlotinib after progression. A total of 146 patients were enrolled. No significant differences in PFS or OS were found between treatment arms.

Pretreatment serum or plasma samples from patients in the LCCC0512 trial were available for VeriStrat testing. 124 samples were received. Sixty four samples were classified as VeriStrat Good, 39 as VeriStrat Poor and 7 as Indeterminate (undefined/equivocal classification). Of the remaining samples 13 could not be processed due to hemolysis and data could not be collected from one sample. For 5 samples where VeriStrat testing was performed, the samples could not be matched to clinical data from the trial. This left 98 samples with VeriStrat classification of Good or Poor and clinical data for statistical analysis. The majority of the samples tested were plasma, but where plasma was not available for a few patients, serum samples were used. Of the samples on which VeriStrat testing yielded a result of Good or Poor only 5 were identified as serum.

Survival analysis was carried out using SAS Enterprise Guide (SAS 9.2). Difference between groups was assessed using log-rank p values. Both univariate and multivariate hazard ratios were evaluated using Cox proportional hazard models. Kaplan-Meier plots and p values for contingency tables were generated using PRISM (GraphPad). For purposes of this disclosure, the data of interest pertain to the "gemcitabine" arm.

Figure 1:
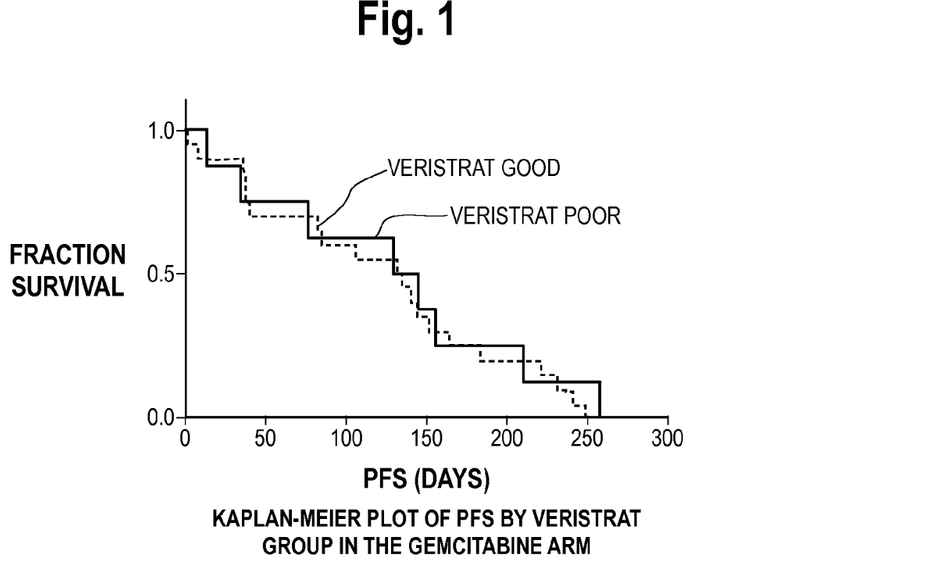
FIG. 1 is a Kaplan-Meier plot of progression free survival (PFS) by VeriStrat group for NSCLC patients treated with gemcitabine alone.

FIG. 1 is a Kaplan-Meier plot of progression free survival (PFS) by VeriStrat ("VS") group for NSCLC patients in the LCCC0512 study treated with gemcitabine alone. Both VeriStrat groups have similar PFS (log-rank p=0.67; hazard ratio (HR)=1.21, 95% Confidence Interval (CI): 0.51-2.88). The median PFS is 137 days (95% CI: 13-210 days) in the VeriStrat Poor group and 133 days (95% CI: 37-164 days) in the VeriStrat Good group.

Figure 2:
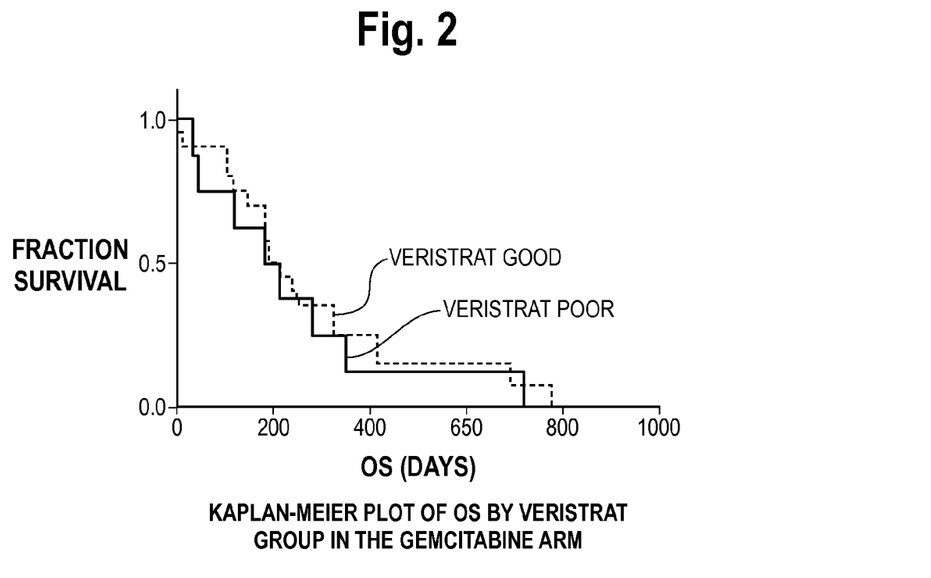
FIG. 2 is a Kaplan-Meier plot of overall survival (OS) by VeriStrat group for NSCLC patients treated with gemcitabine alone.

FIG. 2 is a Kaplan-Meier plot of overall survival (OS) by VeriStrat group for NSCLC patients treated with gemcitabine alone. Both VeriStrat groups have similar OS (log-rank p=0.64; HR=0.82, 95% CI: 0.35-1.90). Median OS is 197 days (95% CI: 34-348 days) in the VeriStrat Poor group and 201 days (95% CI: 119-326 days) in the VeriStrat Good group.

The "Italian study" consisted of the VeriStrat analysis of pretreatment plasma samples from advanced non-small cell lung cancer (NSCLC) patients. The cohort consisted of 33 patients treated at San Raffaele Hospital in Milan, Italy and 112 patients treated in Perugia, Italy. All patients received cisplatin-based chemotherapy as first-line treatment for advanced NSCLC. Patients treated at Perugia were known to have received the specific combination of cisplatin and gemcitabine, while the specific therapy received by patients treated in Milan is not known, only that it is was cisplatin-based. Although the study involved patients with ECOG performance status (PS) 0-3, most patients had PS 0 (43%) or 1 (48%). Most patients (66%) presented with stage IV, metastatic disease, with the remaining patients having stage IIIA or IIIB disease. Eighty three percent of patients were current or former smokers and 79% were male.

VeriStrat testing was performed on plasma samples collected prior to commencement of cisplatin treatment. Of the 145 available samples, 83 (57%) were classified as VeriStrat Good, 58 (40%) as VeriStrat Poor and the remaining 4 samples received the equivocal indeterminate classification (see discussion of FIG. 5 below).

Figure 3:
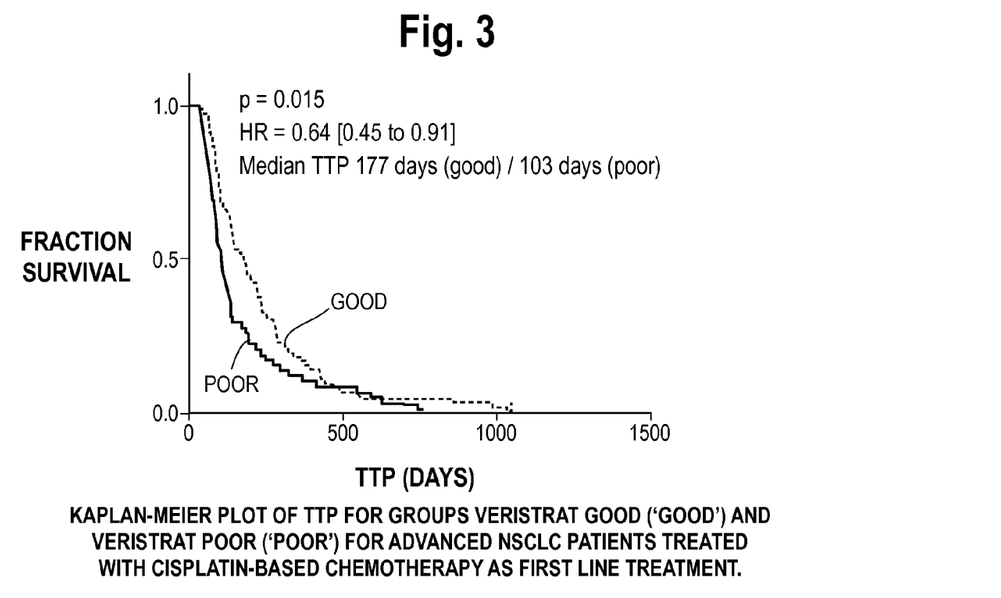
FIG. 3 is a Kaplan-Meier plot of time to progression (TTP) by VeriStrat group for advanced NSCLC patients treated with cisplatin as first line treatment. Most of the patients in the data shown in FIG. 3 were administered gemcitabine in addition to cisplatin.

Time to progression (TTP) in the Italian study was analyzed by VeriStrat classification, see FIG. 3. The VeriStrat Good group had significantly better TTP than the VeriStrat Poor group, hazard ratio (HR)=0.64 (95% CI: 0.45-0.91), log-rank p=0.015. The median TTP in the Good group was 177 days, compared with 103 days in the Poor group.

Figure 4:
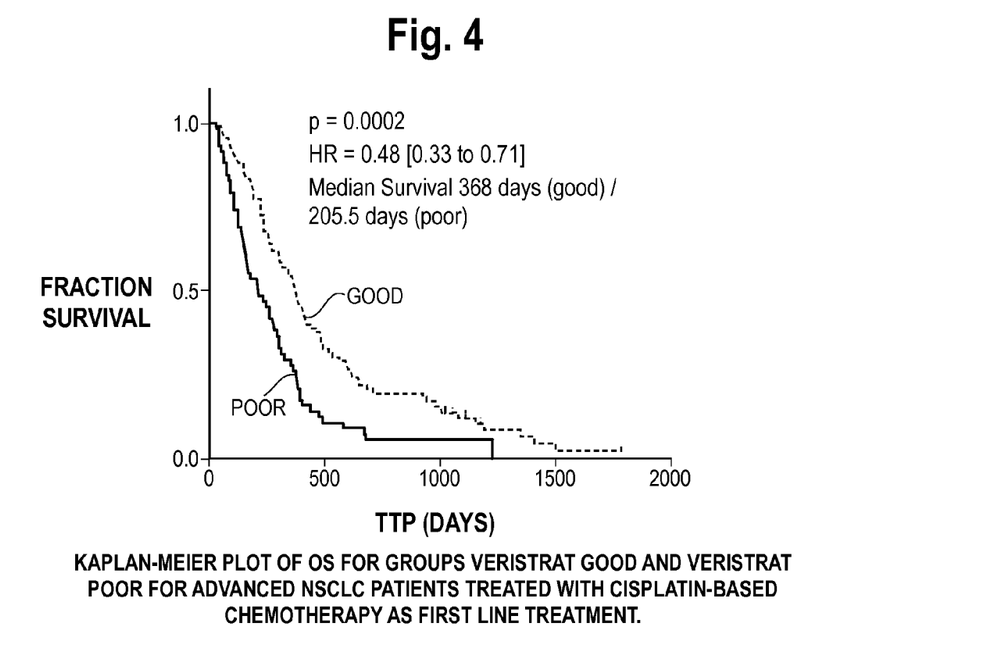
FIG. 4 is a Kaplan-Meier plot of OS by VeriStrat group for advanced NSCLC patients treated with cisplatin as first line treatment. Most of the patients in the data shown in FIG. 4 were administered gemcitabine in addition to cisplatin.

When overall survival (OS) in the Italian study was analyzed by VeriStrat classification, the VeriStrat Good group was found to have significantly longer OS than the VeriStrat Poor group, see FIG. 4. In FIG. 4, the HR=0.48 (95% CI: 0.33-0.71), log-rank p=0.0002. The median survival time was 368 days in the VeriStrat Good group and only 205.5 days in the Poor group.

Analysis of the response to the cisplatin-based chemotherapy showed that response was significantly correlated with VeriStrat classification (p value for chi-squared test=0.049), see Table 1 below. Objective response was significantly correlated with VeriStrat classification (Fisher's exact test p=0.025) with 38% vs. 20% in the evaluable patients classified as VeriStrat Good and Poor respectively. Disease control showed a trend to a significant correlation with VeriStrat classification in patients evaluable for response (67% vs 49% in Good vs Poor).

TABLE 1

Response to cisplatin-based chemotherapy by VeriStrat classification

|  | VeriStrat Good | VeriStrat Poor | P value |
|---|---|---|---|
| PD | 27 | 28 | 0.049 |
| PR | 31 | 11 |  |
| SD | 23 | 16 |  |
| Objective Response - Yes | 31 | 11 | 0.025 |
| Objective Response - No | 50 | 44 |  |
| Disease Control - Yes | 54 | 27 | 0.056 |
| Disease Control - No | 27 | 28 |  |

From the Italian study, we conclude that, when treated with cisplatin-based chemotherapy, VeriStrat Good patients had significantly better TTP and OS than VeriStrat Poor patients. The differences in median TTP and median OS between Good and Poor groups were clinically meaningful, being more than 70 days for TTP and more than 160 days in OS. In addition, objective response rate was significantly greater in the Good group than in the Poor group and there was a strong trend to a similar significantly larger disease control rate.

Furthermore, because most of the patients in the Italian study received the combination of gemcitabine and cisplatin, comparison of the Kaplan-Meier plots of FIGS. 3 and 4 with the Kaplan-Meier plots of the LCCC0512 study (FIGS. 1 and 2) is insightful. When one studies FIGS. 1-4 together, we see that in the treatment arm of gemcitabine+cisplatin the Kaplan-Meier plots show clear separation by VS groups (FIGS. 3 and 4), and in particular in FIG. 4 the VS Poor patients do much worse than the VS Good patients, whereas in the treatment arm of gemcitabine alone the Kaplan-Meier plots show no separation by VS groups at all (FIGS. 1 and 2). Hence, one can conclude that there is likely a differential treatment effect between the two treatments for the VS groups.

Another example of separation of VeriStrat groups treated with platinum-containing therapy was observed in ovarian cancer patients receiving carboplatin and paclitaxel after surgery. See FIGS. 7A and 7B. The data shown in FIGS. 7A and 7B reflect VeriStrat testing on a subset of 96 patients from a larger study of about 160 patients. In this study, serum samples were taken from ovarian cancer patients before surgery and retrospectively analyzed with the VeriStrat test. After surgery, the patients were treated with carboplatin and paclitaxel. The results indicate that patients classified as VeriStrat Poor have shorter disease free survival (FIG. 7A) and shorter overall survival (FIG. 7B) than VeriStrat Good patients when treated with the platinum-based chemotherapy.

Figure 7A:
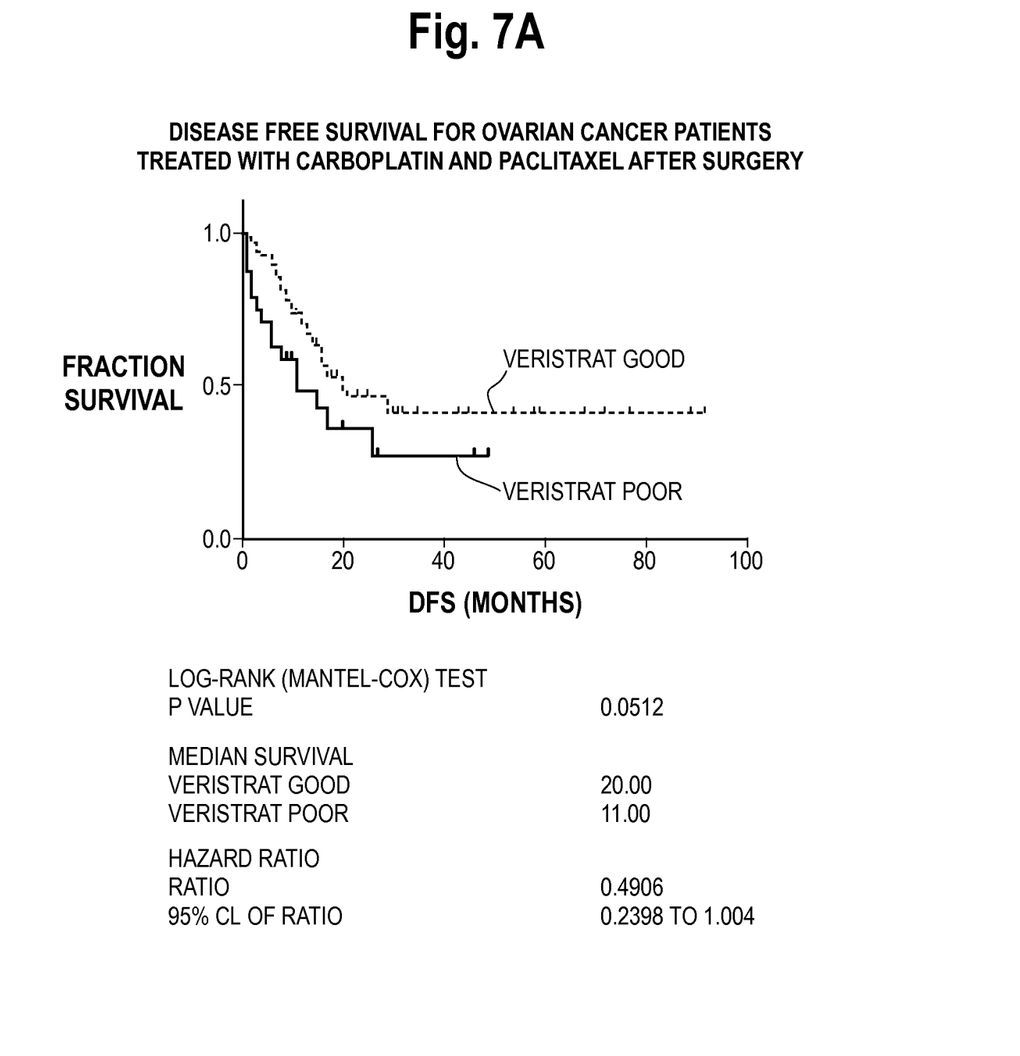
FIGS. 7A and 7B are Kaplan-Meier plots of disease free survival (DFS) and overall survival (OS), respectively, for ovarian cancer patients who, after surgery, were treated with carboplatin and paclitaxel. The results show that patients classified as VeriStrat Poor have shorter disease free survival and overall survival than VeriStrat Good patients when treated with the platinum-based chemotherapy.
Figure 7B:
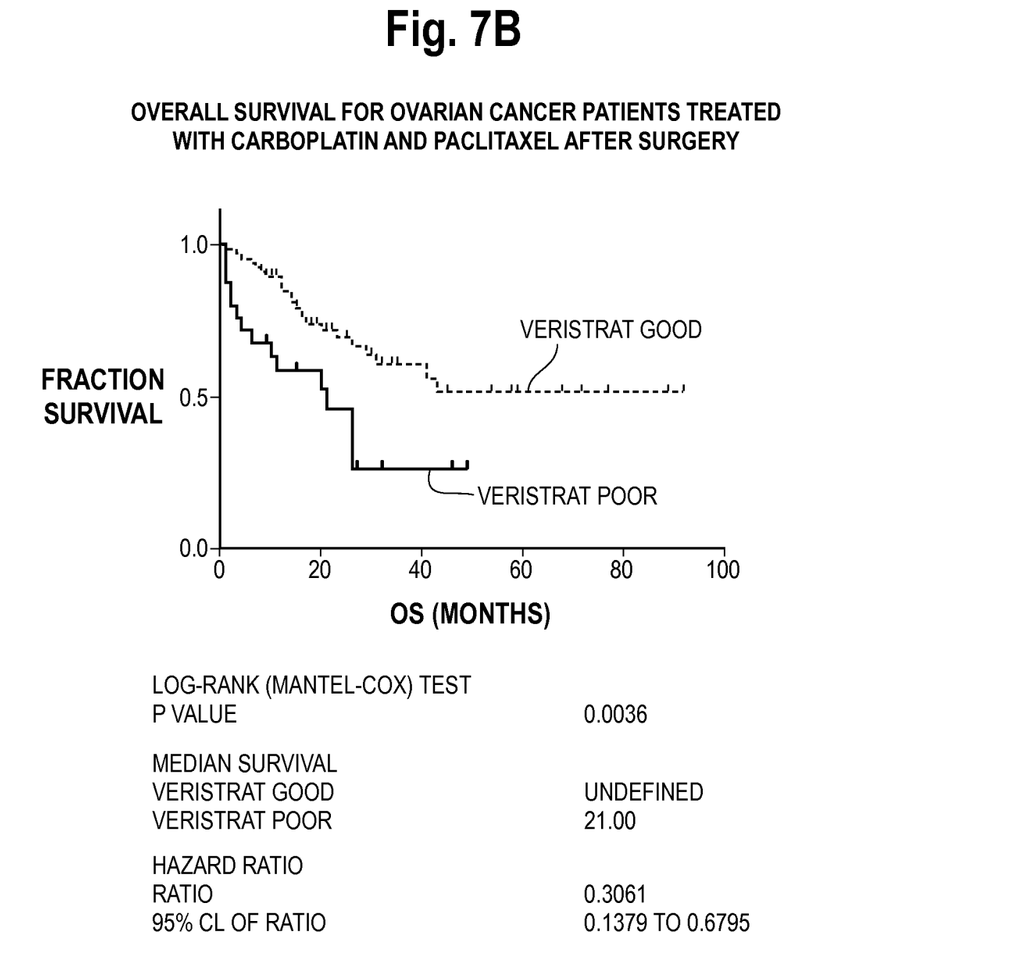

For FIG. 7A, the log-rank (Mantel-Cox) Test P value=0.0512. Median disease free survival times for VeriStrat Good patients was 20 months whereas it was 11 months for VeriStrat Poor patients. The data have a Hazard Ratio of 0.4906 and a 95% Confidence Index (CI) of ratio 0.2398 to 1.004. In FIG. 7B the log-rank Test P value=0.0036, the median overall survival time for VeriStrat Good patients is undefined and for VeriStrat Poor patients is 21 months. The data have a Hazard Ratio of 0.3061 and a 95% Confidence Index (CI) of ratio 0.1379 to 0.6795.

Figure 6:
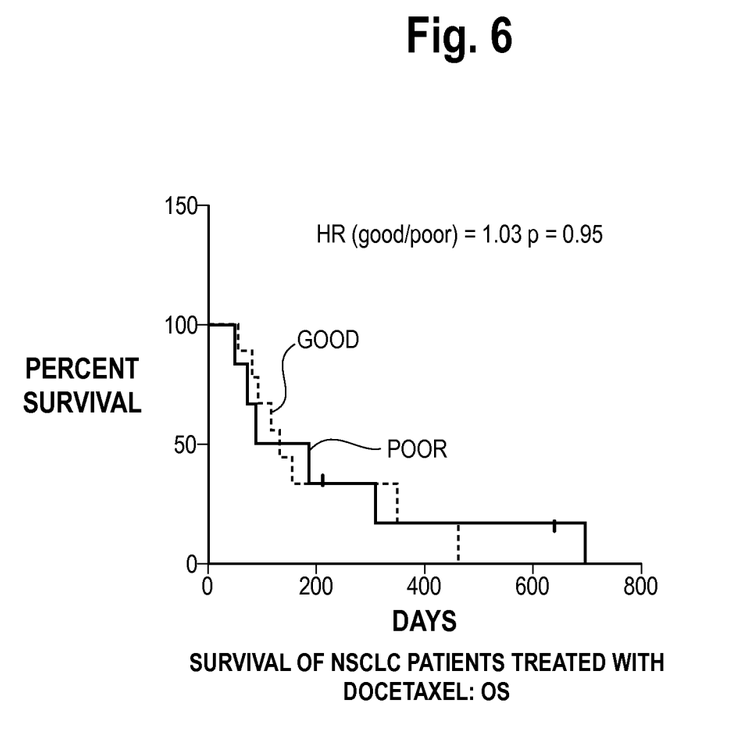
FIG. 6 is a Kaplan-Meier plot of overall survival for a subgroup analysis of one of the cohorts studied in Taguchi et al., Mass spectrometry to classify non-small-cell lung cancer patients for clinical outcome after treatment with epidermal growth factor receptor tyrosine kinase inhibitors: a multicohort cross-institutional study. J Natl Cancer Inst 2007; 99:838-46, showing that NSCLC patients treated with docetaxel exhibit similar overall survival rates regardless of VeriStrat label for such patients.

Given our previous experience with VeriStrat separation in NSCLC and other cancers, we believe that the difference shown in FIGS. 1-4 and 7A-7B lies principally in the Poor group—i.e., that they probably benefit very little from the combination of gemcitabine+cisplatin (or possibly other combinations of chemotherapy based on a platinum agent), but can get outcomes similar to Good patients if they receive gemcitabine alone, or another non-platinum agent, for example, docetaxel. Our results in a subgroup of NSCLC patients treated with docetaxel show no difference in overall survival between VeriStrat Good and VeriStrat Poor patients (hazard ratio 1.03, p=0.95, see FIG. 6 for a Kaplan-Meier plot)

We further believe that VS Poor NSCLC patients are likely to do worse, or certainly no better, on gemcitabine+cisplatin than they would on gemcitabine alone, probably because they do badly on a platinum agent and addition of the gemcitabine does not correct this. On gemcitabine alone VS Poor NSCLC patients do as well as the VS Good patients (FIGS. 1 and 2). Therefore, it can be concluded that the VS Poor class label predicts that the NSCLC patients are not likely to benefit from platinum-based chemotherapy agent (e.g., cisplatin or analogs thereof) either singly or in combination treatments with non-platinum chemotherapy agents.

We further observe that the addition of platinum-based agents to other anticancer therapies that might otherwise help those patients classified as VeriStrat Poor negates the beneficial effects of such non-platinum-based anticancer therapies.

While we cannot exclude the possibility that the VeriStrat Good patients may do better on gemcitabine+cisplatin than gemcitabine alone, we believe the above considerations (in addition to the ovarian cancer data presented in FIGS. 7A and 7B) support the hypothesis that the difference in separation between VeriStrat Good and VeriStrat Poor groups treated with gemcitabine+cisplatin is due to the VeriStrat Poor patients not obtaining benefit from anticancer agents combined with platinum chemotherapy, rather than only the VeriStrat Good patients obtaining benefit from adding cisplatin to gemcitabine.

The VeriStrat Test and Guiding Patient Treatment

As noted above, practical useful tests follow from the discoveries of this disclosure. One aspect is that our testing method identifies whether a particular cancer patient is a member of a group of cancer patients that are not likely to benefit from administration of a platinum-based chemotherapy agent, e.g., cisplatin, carboplatin or analogs thereof, either alone or in combination with other non-platinum chemotherapy agents, e.g., gemcitabine. This identification can be made in advance of treatment.

In one example, a method for guiding treatment of a NSCLC patient is described, comprising the steps of: a) obtaining a blood-based sample from the patient; b) obtaining a mass-spectrum of the blood-based sample with the aid of a mass spectrometer; c) in a programmed computer, performing predefined pre-processing steps on the mass spectrum, obtaining integrated intensity values of selected features in the spectrum over predefined m/z ranges after the pre-processing steps are performed, and comparing the integrated intensity values with a training set comprising class-labeled spectra from other cancer patients and classifying the mass spectrum with a class label, and d) if the class label is Poor or the equivalent, the patient is predicted to not benefit from treatment in the form of administration of a platinum-based chemotherapy agent and is thereby guided towards a treatment regimen not containing platinum agents.

Figure 5:
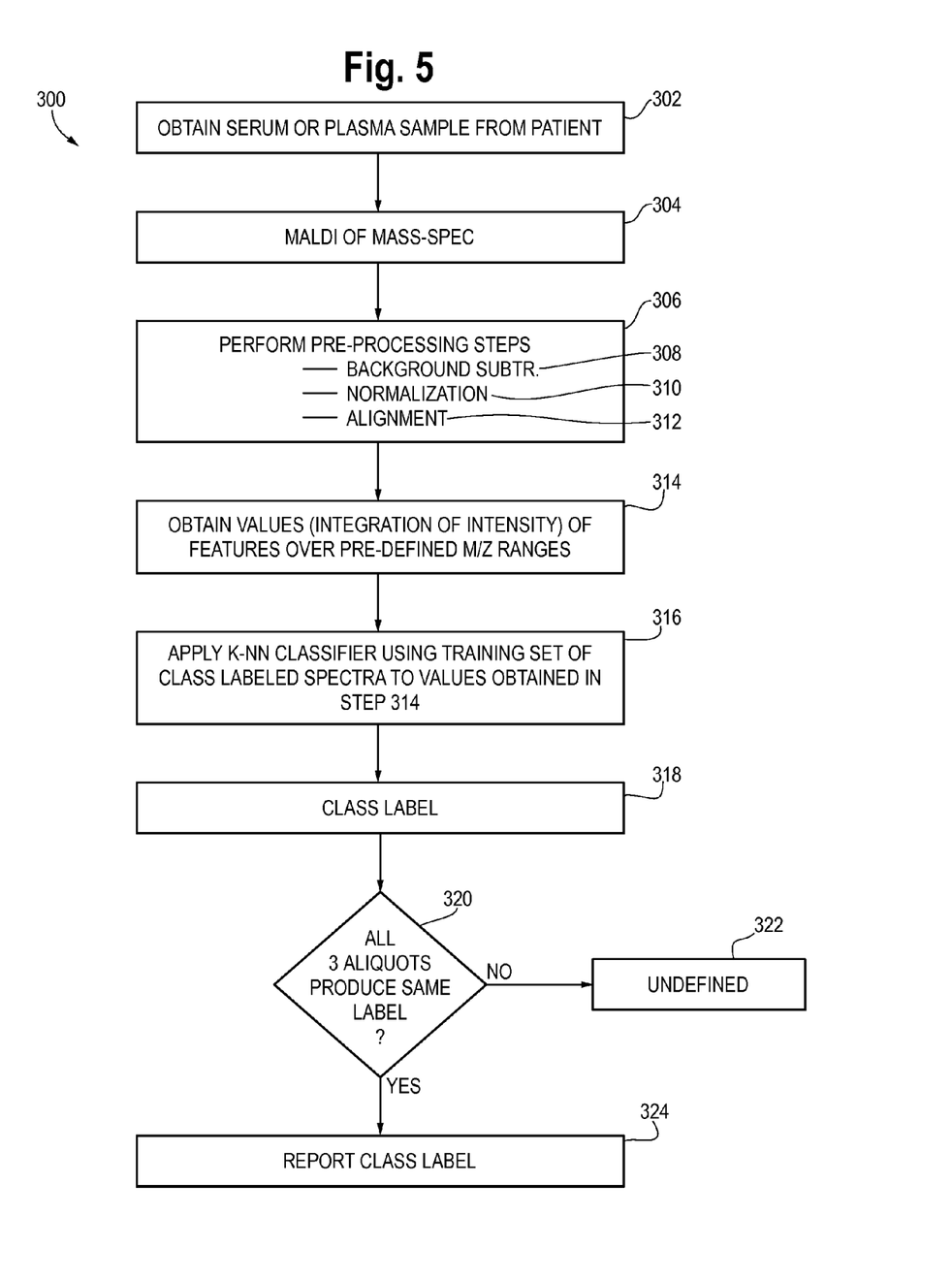
FIG. 5 is a flow-chart of a process for conducting mass spectrometry on a blood-based sample and classifying the spectrum as Good or Poor using a class-labeled training set. If the patient sample is classified under the method as Poor or the equivalent, the patient is predicted to not benefit from platinum-based chemotherapy agents and is guided towards a treatment regimen not containing platinum-based chemotherapy agents.

The test is illustrated in flow chart form in FIG. 5 as a process 300.

At step 302, a serum or plasma sample is obtained from the patient. In one embodiment, the serum samples are separated into three aliquots and the mass spectrometry and subsequent steps 304, 306 (including sub-steps 308, 310 and 312), 314, 316 and 318 are performed independently on each of the aliquots. The number of aliquots can vary, for example there may be 4, 5 or 10 aliquots, and each aliquot is subject to the subsequent processing steps.

At step 304, the sample (aliquot) is subject to mass spectrometry. A preferred method of mass spectrometry is matrix assisted laser desorption ionization (MALDI) time of flight (TOF) mass spectrometry, but other methods are possible. Mass spectrometry produces mass spectra consisting of data points that represent intensity values at a multitude of mass/charge (m/z) values, as is conventional in the art. In one example embodiment, the samples are thawed and centrifuged at 1500 rpm for five minutes at four degrees Celsius. Further, the samples may be diluted 1:10, or 1:5, in MilliQ water. Diluted samples may be spotted in randomly allocated positions on a MALDI plate in triplicate (i.e., on three different MALDI targets). After 0.75 ul of diluted sample is spotted on a MALDI plate, 0.75 ul of 35 mg/ml sinapinic acid (in 50% acetonitrile and 0.1% trifluoroacetic acid (TFA)) may be added and mixed by pipetting up and down five times. Plates may be allowed to dry at room temperature. It should be understood that other techniques and procedures may be utilized for preparing and processing samples in accordance with the principles of the present invention.

Mass spectra may be acquired for positive ions in linear mode using a Voyager DE-PRO or DE-STR MALDI TOF mass spectrometer with automated or manual collection of the spectra. (Of course, other MALDI TOF instruments could be used, e.g., instruments of Bruker Corporation). Seventy five or one hundred spectra are collected from seven or five positions within each MALDI spot in order to generate an average of 525 or 500 spectra for each sample specimen. Spectra are externally calibrated using a mixture of protein standards (Insulin (bovine), thioredoxin (*E. coli*), and Apomyglobin (equine)).

At step 306, the spectra obtained in step 304 are subject to one or more pre-defined pre-processing steps. The pre-processing steps 306 are implemented in a general purpose computer using software instructions that operate on the mass spectral data obtained in step 304. The pre-processing steps 306 include background subtraction (step 308), normalization (step 310) and alignment (step 312). The step of background subtraction preferably involves generating a robust, asymmetrical estimate of background in the spectrum and subtracts the background from the spectrum. Step 308 uses the background subtraction techniques described in U.S. Pat. No. 7,736,905, which is incorporated by reference herein. The normalization step 310 involves a normalization of the background subtracted spectrum. The normalization can take the form of a partial ion current normalization, or a total ion current normalization, as described in U.S. Pat. No. 7,736, 905. Step 312 as described in U.S. Pat. No. 7,736,905 aligns the normalized, background subtracted spectrum to a pre-defined mass scale, which can be obtained from investigation of the training set used by the classifier.

Once the pre-processing steps 306 are performed, the process 300 proceeds to step 314 of obtaining integrated intensities in the spectrum over predefined m/z ranges. The normalized and background subtracted intensity values may be integrated over these m/z ranges. This integrated value (i.e., the sum of intensities within the corresponding predefined m/z range is assigned to a feature. Predefined m/z ranges may be defined as the interval around the average m/z position of the corresponding feature with a width corresponding to the peak width at this m/z position. This step is also disclosed in further detail in U.S. Pat. No. 7,736,905.

At step 314, the integrated values of intensities in the spectrum are obtained at one or more of the following m/z ranges:
5732 to 5795
5811 to 5875
6398 to 6469
11376 to 11515
11459 to 11599
11614 to 11756
11687 to 11831
11830 to 11976
12375 to 12529
12502 to 12656
23183 to 23525
23279 to 23622 and
65902 to 67502.

In a preferred embodiment, values are obtained at eight of these m/z ranges shown in Table 2 below. The significance, and methods of discovery of these peaks, is explained in the U.S. Pat. No. 7,736,905. In practice the above widths (ranges) may vary.

At step 316, the values obtained at step 314 are supplied to a classifier, which in the illustrated embodiment is a K-nearest neighbor (KNN) classifier. The classifier makes use of a training set of class labeled spectra from a multitude of other patients (which may be NSCLC cancer patients, or other solid epithelial cancer patients, e.g., HNSCC, breast cancer). The application of the KNN classification algorithm to the values at 314 and the training set is explained in U.S. Pat. No. 7,736,905. Other classifiers can be used, including a probabilistic KNN classifier or other classifier. In the illustrated embodiment, the training set is in the form of class-labeled spectra from NSCLC patients that either did or did not benefit from administration of EGFR inhibitors, those that did benefit being labeled "Good" and those that did not labeled "Poor."

At step 318, the classifier produces a label for the spectrum, either Good, or Poor. As mentioned above, steps 304-318 are performed in parallel on the three separate aliquots from a given patient sample (or whatever number of aliquots are used). At step 320, a check is made to determine whether all the aliquots produce the same class label. If not, an undefined (or Indeterminate) result is returned as indicated at step 322. If all aliquots produce the same label, the label is reported as indicated at step 324.

As described in this document, new and unexpected uses of the class label reported at step 324 are disclosed. For example, those NSCLC cancer patients labeled Poor in accordance with the VeriStrat test are unlikely to benefit from treatment in the form of a platinum-based chemotherapy agent, such as cisplatin or analogs thereof. As another example, if the NSCLC patient is identified as Poor in accordance with the test, then the patient is not likely to benefit from administration of a combination of a platinum-based chemotherapy agent and a non-platinum-based chemotherapy agent, such as the combination of gemcitabine and cisplatin.

It will be understood that steps 306, 314, 316 and 318 are typically performed in a programmed general purpose computer using software coding the pre-processing steps 306, the obtaining of integrated intensity values in step 314, the application of the KNN classification algorithm in step 316 and the generation of the class label in step 318. The training set of class labeled spectra used in step 116 is stored in memory in the computer or in a memory accessible to the computer.

The method and programmed computer may be advantageously implemented at a laboratory test processing center as described in our prior patent application publication U.S. Pat. No. 7,736,905.

TABLE 2

Peaks used in VeriStrat.

| Peak number | m/z |
|---|---|
| 1 | 5843 |
| 2 | 11445 |
| 3 | 11529 |
| 4 | 11685 |
| 5 | 11759 |
| 6 | 11903 |
| 7 | 12452 |
| 8 | 12579 |

It will further be noted that step 304, conducting MALDI-TOF mass spectrometry on the sample, can be performed in accordance with the so-called "deep-MALDI" methods of conducting mass spectrometry as described in U.S. provisional application Ser. No. 61/652,394 filed May 29, 2012, the entire content of which is incorporated by reference herein. Additionally, the features used for classification may be obtained by investigation of spectra obtained from a multitude of samples subject to the "deep-MALDI" method as well.

Generalization of the VeriStrat test as predictive of patient non-benefit from platinum-based chemotherapy to other cancers, including HNSCC (head and neck cancer), ovarian, CRC, breast and others.

The VeriStrat Poor signature has been found in many different epithelial cancer types, including NSCLC, squamous cell carcinoma of the head and neck (SSCHN, or HNSCC), colorectal cancer, renal cell carcinoma, melanoma, pancreatic cancer, breast cancer and ovarian cancer, but has not been identified in patients without cancer. Hence, while not specific to lung cancer, it is related to the patient's cancer. In the absence of systemic treatment, patients classified as VeriStrat Poor have inferior outcomes (in terms of OS and PFS) as compared to patients classified at VeriStrat Good (Carbone D. et al., 2nd European Lung Cancer Conference, April 2010. J Thorac Oncol 2010; 5(5) S80 abstr. 203O) and hence VeriStrat Poor classification is measuring an innate property of the disease, or specific disease state.

In addition to its prognostic capability, the VeriStrat test has demonstrated a significant predictive power, the ability to predict differential treatment benefit between VeriStrat groups, in multiple trials across multiple tumor types, including NSCLC and breast cancer, including the studies mentioned in this application and in EGF30008, see U.S. patent application Ser. No. 13/356,730 filed Jan. 24, 2012.

Previous studies have shown that separation in outcomes between VeriStrat groups depends on the treatment regimen, but is not restricted to the type of cancer. For example, VeriStrat Good patients have been shown to have better progression-free survival and overall survival than VeriStrat Poor patients when treated with EGFR inhibitors not only when they have NSCLC, but also when they have SSCHN or colorectal cancer (see, e.g., the previous patent literature of Biodesix, Inc. cited above, and Cancer Epidemiol Biomarkers Prev. 2010 February; 19 (2):358-65; Taguchi F. et al., J. Nat. Cancer Institute, 2007 v. 99 (11), 838-846); Chung C, Seeley E, Roder H, et al. Detection of tumor epidermal growth factor receptor pathway dependence by serum mass spectrometry in cancer patients. Cancer Epidemiol Biomarkers Prev. 2010 February; 19 (2):358-65). Similarly, we have data in other treatment regimens across tumor types where there is no separation between VeriStrat groups, e.g. non-platinum based chemotherapy in HNSCC (Chung et al. article, supra) and NSCLC (Stinchcombe, T. E. et al. A randomized phase II trial of first-line treatment with gemcitabine, erlotinib, or gemcitabine and erlotinib in elderly patients (age>/=70 years) with stage IIIB/IV non-small cell lung cancer. J Thorac Oncol 6, 1569-77 (2011).

On the basis of this body of evidence over many tumor types, we hypothesize that pretreatment VeriStrat Poor status is identifying a specific disease state across tumor types and that there are classes of therapies where we observe inferior outcomes for VS Poor patients across tumor types (e.g. EGFRI monotherapy) and others where we observe similar outcomes for both VS groups (e.g. non-platinum chemotherapy). This leads us to conclude that it is likely that the inferior outcomes observed in NSCLC patients treated with a chemotherapy regimen containing a platinum-based agent, will not be unique to NSCLC, but rather should be expected in all cancer types where we observe VeriStrat Poor patients and platinum-based chemotherapy is used.

We claim:

1. A method for guiding treatment of a cancer patient, comprising the steps of:
   a) obtaining a blood-based sample from the patient;
   b) obtaining a mass-spectrum of the blood-based sample with the aid of a mass spectrometer;
   c) in a programmed computer, performing predefined pre-processing steps on the mass spectrum, obtaining integrated intensity values of selected features at one or more predefined m/z ranges in the spectrum after the pre-processing steps are performed and comparing the integrated intensity values with a training set comprising class-labeled spectra from blood-based samples of other cancer patients and classifying the mass spectrum with a class label, and
   d) if the class label is Poor or the equivalent, the patient is predicted, in advance, to not benefit from treatment in the form of administration of a platinum-based chemotherapy agent and is thereby guided towards a treatment regimen not containing platinum agents;
   wherein the predefined m/z ranges are contained within m/z ranges selected from the group of m/z ranges consisting of:

5811 to 5875
6398 to 6469
11376 to 11515
11459 to 11599
11614 to 11756
11687 to 11831
11830 to 11976
12375 to 12529
12502 to 12656
23183 to 23525
23279 to 23622
65902 to 67502.

2. The method of claim 1, wherein in step d) if the class label is Poor or the equivalent, the patient is predicted to not benefit from treatment in the form of administration of a combination of a non-platinum chemotherapy agent and a platinum-based chemotherapy agent and the patient is guided towards treatment regimen not containing platinum agents.

3. The method of claim 1, wherein the platinum-based chemotherapy agent comprises cisplatin, carboplatin or analogs thereof.

4. The method of any of claim 1, wherein the treatment regimen not containing platinum agents comprises gemcitabine or the analog or docetaxel or the analog, and wherein the platinum-based chemotherapy agent comprises cisplatin or analogs thereof.

5. The method of claim 1, wherein the training set comprises class-labeled spectra from non-small cell lung cancer (NSCLC) patients, the class labels indicating whether the patients obtained benefit from treatment by administration of an epidermal growth factor receptor inhibitor, the class label Poor assigned to members in the training set for those NSCLC patients that did not benefit from the administration of an epidermal growth factor receptor inhibitor.

6. The method of claim 1, wherein the cancer patient comprises a patient having either ovarian cancer or non-small cell lung cancer.

7. The method of claim 6, wherein the platinum-based chemotherapy agent comprises cisplatin, carboplatin or analogs thereof.

8. The method of claim 6, wherein the treatment regimen not containing platinum agents comprises gemcitabine or the analog or docetaxel or the analog, and wherein the platinum-based chemotherapy agent comprises cisplatin or analogs thereof.

9. The method of claim 6, wherein the training set comprises class-labeled spectra from non-small-cell lung cancer (NSCLC) patients, the class labels indicating whether the patients obtained benefit from treatment by administration of an epidermal growth factor receptor inhibitor, the class label Poor assigned to members in the training set for those NSCLC patients that did not benefit from the administration of an epidermal growth factor receptor inhibitor.

10. The method of claim 1, wherein the cancer patient has either colorectal cancer or head and neck cancer.

* * * * *